United States Patent
Nigam et al.

(10) Patent No.: US 7,071,356 B1
(45) Date of Patent: Jul. 4, 2006

(54) PROCESS FOR THE PREPARATION OF 1-(AMINOMETHYL) CYCLOHEXANEACETIC ACID

(75) Inventors: Satish C. Nigam, Hilliard, OH (US); Krishnamurthy Nacharaju, Hilliard, OH (US); Christophe Buron, Columbus, OH (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 11/291,604

(22) Filed: Dec. 1, 2005

(51) Int. Cl.
*C07C 61/06* (2006.01)
(52) U.S. Cl. .................................. 562/507
(58) Field of Classification Search ............... 562/507
See application file for complete search history.

(56) References Cited

U.S. PATENT DOCUMENTS 6,255,526 B1   7/2001 Pesachovich et al. ....... 562/507
6,518,456 B1   2/2003 Peverali et al. ............. 562/507
6,521,788 B1   2/2003 Velardi et al. .............. 562/507
6,846,950 B1   1/2005 Ferrari et al. .............. 562/507
2004/0034248 A1   2/2004 Bercovici et al. ........... 562/507
2005/0049432 A1   3/2005 Ferrari et al. .............. 562/507

FOREIGN PATENT DOCUMENTS

WO    WO 03/070683    8/2003

*Primary Examiner*—Samuel Barts
(74) *Attorney, Agent, or Firm*—William J. Davis; Imre Balogh

(57) ABSTRACT

A method of producing gabapentin (1-amino-methyl)-1-cyclohexaneacetic acid) from its hydrochloric salt in an anhydrous medium, the method consisting of:
dissolving gabapentin hydrochloride in a non-aqueous organic solvent in which gabapentin is insoluble to obtain a solution of gabapentin hydrochloride;
adding an epoxide to the solution to remove the chloride ions thereby precipitating gabapentin out of the solution as a white solid;
recovering the white solid by filtration; and
drying the white solid.

8 Claims, No Drawings

PROCESS FOR THE PREPARATION OF 1-(AMINOMETHYL) CYCLOHEXANEACETIC ACID

BACKGROUND OF THE INVENTION

1. Field of the Invention

The present invention relates to an economical process for producing gabapentin from its hydrochloride salt in an anhydrous medium directly in the desired form having the structural formula:

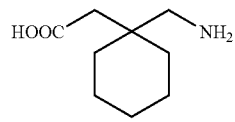

2. Reported Developments

Gabapentin is known in the prior art and is used in the treatment of cerebral diseases including epilepsy, hypokinesia, and cranial trachmas. Various methods are described in the art of the synthesis and/or purification of gabapentin and related compounds. Examplary references include the following.

U.S. Pat. No. 6,255,526 discloses a method for purifying gabapentin by converting gabapentin hydrochloride salt to gabapentin by:

reacting a solution of gabapentin hydrochloride with an amine in a first solvent to produce a polymorphic form III as a precipitate;

converting the polymorphic form to form II by recrystallization of the precipitate in methanol; and recovering gabapentin form II.

WO 03/070683 discloses a process for preparing mineral acid addition salts of gabapentin comprising:

treating cyclohexane diacetic acid monoamide with sodium hypobromide;

acidifying the reaction mass;

extracting the acid addition salt with hydrocarbon solvent containing a carbonyl group;

evaporating and dissolving the extract in alcohol solvent;

filtering the undissolved material and evaporating the alcohol solvent to obtain a syrupy residue; and mixing the residue with non-polar organic solvents to obtain mineral acid addition salts of gabapentin.

U.S. Pat. No. 6,518,456 discloses a process for the production and purification of gabapentin comprising:

hydrolysis of 2-aza-spiro[4.5] decan-3-one with HCl;

treatment of the resulting product with acetone and filtration; and dissolution with water neutralization and crystallization on digestion in mixtures of di-isopropyl ether with ethanol or methanol.

U.S. Pat. No. 6,521,788 discloses a process of producing gabapentin comprising:

a) reduction of (1-nitromethyl-cyclohexyl)acetonitrile of formula (II):

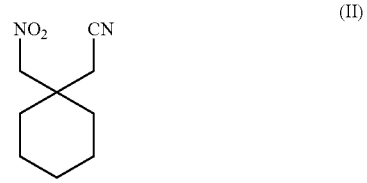

to give 3-imino-2-azaspiro[4.5]decan-2-ol of formula III

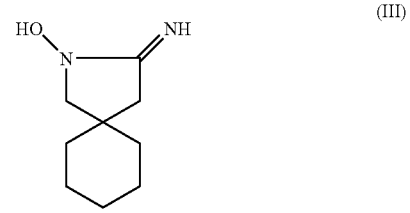

b) transformation of compound (III) by alkali treatment, into 2-hydroxy-2-aza-spiro[4.5]decan-3-one of formula (IV)

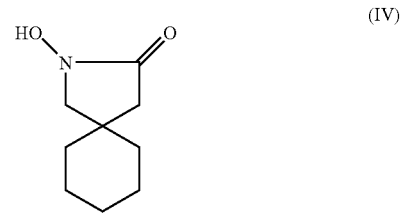

c) reduction of compound (IV) to give 2-aza-spiro[4.5]decan-3-one of formula (V)

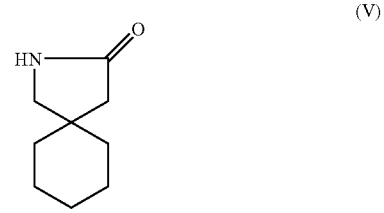

and d) hydrolysis of compound (V) to gabapentin.

U.S. Patent Application No. 2004/0034248 discloses compositions and methods of preparing gabapentin that include: (a) subjecting cyclohexanediacetic acid monoamide to a Hofmann rearrangement to yield a solution comprising an isocyanate intermediate; (b) hydrolyzing the isocyanate intermediate in the presence of an alkali base to form a gabapentin alkali salt; (c) converting the gabapentin alkali salt to a gabapentin-amine salt in a water-miscible polar solvent; (d) adding a basic or weakly basic ion exchange resin to a solution comprising the gabapentin-amine salt; (e) removing the ion exchange resin from the solution; and (f) concentrating the solution to yield gabapentin.

U.S. Pat. No. 6,846,950 discloses a process for synthesizing gabapentin hydrochloride comprising:

reacting a mixture of acetic anhydride/ammonium acetate with 1,1-cyclohexane-diacetic acid to yield 3,3-pentamethylene glutarimide;

treating 3,3-pentamethylene glutarimide with sodium hydroxide in an aqueous solution up to dissolution;

dripping the solution into a sodium hydroxide/sodium hypochlorite mixture; and acidifying the mixture with hydrochloric acid to yield gabapentin hydrochloride.

U.S. Patent Application No. 2005/0049432 discloses a process for the preparation of 1-(aminomethyl)cyclohexane-acetic acid comprising:

dissolving gabapentin hydrochloride in a solvent in which the gabapentin hydrochloride and gabapentin are soluble; and adding an amine that allows the removal of the chloride ion from the solution by precipitation of the chloride ion from the solution, by precipitation of the hydrochloride of the same amine, leaving the gabapentin in solution in free amino acid form.

Some of these and other methods, although used commercially, suffer from various disadvantages particularly while regenerating the gabapentin from its mineral addition salts including:

1. The rejuvenation of gabapentin from its mineral salts using Anion exchange resin in aqueous media is cumbersome, utilizes large chromatographic columns and other specialized costly equipment including regeneration of the resin;

The isolation of amino acids from aqueous solution is time consuming and requires high energy;

2. Using amines, the amine hydrochloride needs to be filtered and neutralized back for recycling; and The regeneration of gabapentin from its addition salts using organic bases requires multiple solvents.

SUMMARY OF THE INVENTION

The present invention provides a simple procedure for generating gabapentin from gabapentin hydrochloride, which heretofor is unknown in the prior art. The process comprises:

1) Dissolving of gabapentin hydrochloride in non-aqueous/organic solvents, preferably alcohols, such as methanol, ethanol, isopropyl alcohol, butanol or mixtures thereof to obtain a solution. The solvents are so chosen that the gabapentin hydrochloride is soluble in the solvents but the gabapentin is not soluble in the solvents;
2) Adding an epoxide, such as ethylene oxide, propylene oxide or 1,2-epoxybutane to the solution. The hydrochloride reacts with the oxide and opens up the ring and in the process releases the gabapentin in its free amino acid form;
3) The reaction in step 2 is carried out at about 0°–50° C., and preferably at about 10°–25° C.;
4) Gabapentin is then precipitated out of the solution.

The advantages being:

1. Cheap raw materials that need to be recovered or recycled
2. Simple and easy operable conditions 3. Anhydrous conditions that prevent recovery from water
4. High purity product.

DETAILED DESCRIPTION OF THE INVENTION

The following exemplifies the synthesis of gabapentin according to the present invention.

EXAMPLE 1

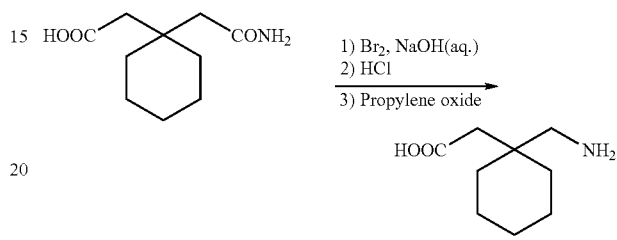

Gabapentin hydrochloride (241 mmol) was solubilized in 200 ml of n-butanol. Propylene oxide was then added to the reaction mixture in one portion. The mixture was stirred for 10–16 hours at 25° C. A white precipitate of gabapentin was observed. The reaction mixture was cooled to 0–5° C. The white solid was recovered by filtration and partially dried under suction. The solid was then rinsed with 50 mL fresh cold n-butanol and dried under suction. The solid was finally dried (50° C., 20–30 mmHg or higher vacuum) overnight or until no loss of weight is observed.

Gabapentin (37.1 g) was obtained in 90% yield that was 99.4% by HPLC.

EXAMPLE 2

Gabapentin hydrochloride (72 mmol) was suspended in 50 mL of isopropyl alcohol and heated gently until complete dissolution. The solution was cooled below 10° C. and propylene oxide (144 mmol) was added in one portion. The mixture was stirred for 16 hours below 10° C., after which it was cooled to −5° C. Pure gabapentin was recovered by filtration and washed with cold isopropanol. Drying at 40–50° C. under reduced pressure afforded 9.4 g of pure gabapentin.

EXAMPLE 3

Gabapentin hydrochloride (72 mmol) was suspended in 50 mL of n-butanol and heated gently until complete dissolution. The solution was cooled below 10° C. and propylene oxide (144 mmol) was added in one portion. The mixture was stirred for 16 hours below 10° C., after which it was cooled to −5° C. Pure gabapentin was recovered by filtration and washed with cold isopropanol. Drying at 40–50° C. under reduced pressure afforded 11.1 g of pure gabapentin.

EXAMPLE 4

Gabapentin hydrochloride (72 mmol) was suspended in 50 mL of methanol and heated gently until complete dissolution. The solution was cooled below 10° C. and propylene oxide (144 mmol) was added in one portion. The mixture was stirred for 16 hours below 10° C., after which it was cooled to −5° C. Pure gabapentin was recovered by filtration and washed with cold isopropanol. Drying at 40–50° C. under reduced pressure afforded 5.5 g of pure gabapentin.

EXAMPLE 5

Gabapentin hydrochloride (72 mmol) was suspended in 50 mL of n-butanol and heated gently until complete dissolution. The solution was cooled below 10° C. and 1,2-epoxybutane (144 mmol) was added in one portion. The mixture was stirred for 16 hours below 10° C., after which it was cooled to −5° C. Pure gabapentin was recovered by filtration and washed with cold isopropanol. Drying at 40–50° C. under reduced pressure afforded 9.4 g of pure gabapentin.

EXAMPLE 6

Gabapentin hydrochloride (72 mmol) was suspended in 50 mL of n-butanol and heated gently until complete dissolution. The solution was cooled below 110° C. and ethylene oxide (144 mmol) was added in one portion. The mixture was stirred for 16 hours below 10° C., after which it was cooled to −5° C. Pure gabapentin was recovered by filtration and washed with cold isopropanol. Drying at 40–50° C. under reduced pressure afforded 9.6 g of pure gabapentin. Same as Example 2, but ethylene was used instead of propylene oxide 9.6 g were recovered.

EXAMPLE 7

Gabapentin hydrochloride (72 mmol) was suspended in 50 mL of isopropyl alcohol and heated gently until complete dissolution. The solution was cooled below 10° C. and 1,2-epoxybutane (144 mmol) was added in one portion. The mixture was stirred for 16 hours below 10° C., after which it was cooled to −5° C. Pure gabapentin was recovered by filtration and washed with cold isopropanol. Drying at 40–50° C. under reduced pressure afforded 9.5 g of pure gabapentin.

EXAMPLE 8

Gabapentin hydrochloride (72 mmol) was suspended in 50 mL of isopropyl alcohol and heated gently until complete dissolution. The solution was cooled below 10° C. and propylene oxide (144 mmol) was added in one portion. The mixture was stirred for 16 hours below 10° C., after which it was cooled to −5° C. Pure gabapentin was recovered by filtration and washed with cold isopropanol. Drying at 40–50° C. under reduced pressure afforded 9.7 g of pure gabapentin.

What is claimed is:

1. A process for the preparation of gabapentin from gabapentin hydrochloride comprising:
   dissolving gabapentin hydrochloride in a non-aqueous organic solvent to obtain a solution;
   adding an epoxide to the solution to remove the chloride ions from the solution thereby precipitating gabapentin out of the solution as a white solid in its free amino acid form;
   recovering the white solid by filtration; and
   drying the white solid until no loss of weight is observed.

2. The process of claim 1 wherein the gabapentin hydrochloride is soluble in the solvent while the gabapentin is not soluble therein.

3. The process according to claim 1 wherein said non-aqueous organic solvent is selected from the group consisting of: methanol, ethanol, isopropyl alcohol and n-butanol.

4. The process of claim 1 wherein said epoxide is selected from the group consisting of ethylene oxide, 1,2-epoxybutane, and propylene oxide.

5. The process of claim 1 wherein said hydrochloride reacts with said oxide opens up the ring in the molecule and releases the gabapentin in its free amino acid form.

6. The process of claim 1 wherein the reaction of said oxide and said hydrochloride is carried out at a temperature of about 0°–50° C.

7. The process of claim 6 wherein said reaction is carried out at about 10°–25° C.

8. The process of claim 1 wherein said dried solid of gabapentin is at least about 99.0% pure.

\* \* \* \* \*